(12) United States Patent
Fattman

(10) Patent No.: US 6,746,765 B1
(45) Date of Patent: Jun. 8, 2004

(54) HYDROCOLLOID ADHESIVE TAPE

(75) Inventor: George F. Fattman, Mount Laurel, NJ (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 10/349,793

(22) Filed: Jan. 23, 2003

(51) Int. Cl.⁷ .............................. B32B 7/12; B32B 5/18
(52) U.S. Cl. ........................ 428/355 N; 428/355 CN; 428/336; 428/315.7; 428/317.5; 428/317.7
(58) Field of Search .................... 428/315.7, 315.9, 428/317.5, 317.7, 336, 339, 343, 352, 355 R, 356, 355 CP, 355 CN, 355 N, 332; 525/191

(56) References Cited

U.S. PATENT DOCUMENTS 4,427,737 A  *  1/1984  Cilento et al. ........... 428/315.7

* cited by examiner

Primary Examiner—James J. Seidleck
Assistant Examiner—Thao Tran
(74) Attorney, Agent, or Firm—Stuart E. Krieger

(57) ABSTRACT

The invention is a thin, occlusive adhesive tape comprised of hydrocolloid powders dispersed in an elastomeric matrix and suitable for attachment to human skin.

10 Claims, No Drawings

HYDROCOLLOID ADHESIVE TAPE

FIELD OF THE INVENTION

The present invention relates to a hydrocolloid adhesive tape useful in ostomy, wound and skin care applications.

BACKGROUND

As a result of a variety of medical conditions it may be in the best interests of the health of an individual to undergo ostomy surgery. In this procedure portion of the intestine or urinary tract is drawn through an opening made in the abdomen (stoma) and then sutured to the skin. Typically an odor-proof pouch is attached to the body to collect effluent from the stoma. Often this attachment is accomplished using an ostomy wafer that has been taken from a planar slab of adhesive and cut to fit the wearer. Attachment of a pouch to the wafer completes the device for collection of fecal or urinary output. Hydrocolloid adhesives of the type described by U.S. Pat. Nos. 3,339,546 or 4,551,490 have been demonstrated to be especially suited to this purpose since their unique ability to absorb moisture enables them to remain securely adhered to the skin for wearing times of up to a week or more.

Security of the device is a critical need of the ostomate because if the adhesive should fail even partially then effluent from the stoma will have an opportunity to attack the peristomal skin causing it to break down rapidly. It is known by those skilled in the art that the security of an ostomy adhesive depends strongly on its thickness. Thicker adhesives adhere more strongly. It is also desirable to have a thick adhesive next to the stoma to protect the peristomal skin. Thicker adhesives resist the corrosiveness of stoma output better than thin adhesives. Additionally, the overall wearing time of the adhesive will be longer for thicker adhesive. Hydrocolloid adhesives rely on absorbency to manage perspiration and remain attached to the skin of the wearer. The absorbing capacity of the device depends on the amount of hydrocolloid powders available. Thicker devices have more hydrocolloids per area of attachment and so remain viable on the skin for longer periods of time.

It is also known by those skilled in the art of hydrocolloid adhesives that several practical considerations limit how thick the adhesive can be. For example, the comfort of the wearer will be greatly improved if the adhesive can be made thin. Thin adhesives are more flexible. They feel lighter when worn. They also conform better to the abdomen as it twists and stretches in the normal course of everyday activities. Because thinner adhesives are less obvious they fulfill another important need of the wearer, discretion. Thinner adhesives also avoid the tendency of thick adhesives to lift at the edges. While a thick adhesive will strongly resist lifting at its center the same rigidity that helps it remain well attached at that point may also cause it to lift slightly along its perimeter. One final reason why thick adhesives are not always optimal is their tendency to leave more residue on the skin than thinner adhesives do.

For secure attachment to the skin it can be seen that thicker adhesives have several advantages. However, they also have drawbacks that can be addressed by reducing their thickness. A balance is required that considers the specific needs of the intended application. For an ostomy device, security is paramount. With the invention of hydrocolloid adhesives came the design of new ostomy products to take advantage of their superiority adhesive technology for this challenging application. Ostomy wafers for these products were designed to be thick to ensure that they would remain well adhered and achieve a long and consistent wear time. For this reason most ostomy wafers in the marketplace typically range in thickness from about 0.040 to 0.100 inch.

As development of ostomy devices progressed it was recognized that a composite wafer could be designed to be thick around the stoma and thin at the edges. U.S. Pat. No. 4,775,374 discloses such a device. In that patent a number of examples are described wherein a relatively thick disc of hydrocolloid adhesive is surrounded by a thinner tape-like adhesive attached at its perimeter. The advantage of this design is that the thicker adhesive provides the area around the stoma with secure adhesion, peristomal skin protection, and adequate absorption capacity for long wear times. The thinner adhesive at its edges prevents edge lifting, helps to minimize residue on the skin, and provides an overall lightness and flexibility that is dramatically more comfortable to wear.

The value of combining thick and thin adhesive profiles in the same ostomy device as disclosed in U.S. Pat. No. 4,775,374 has been confirmed by a number of other patents that have disclosed alternative methods to make adhesive wafers with variable adhesive thickness. For example, U.S. Pat. No. 5,074,852 discloses a composite wafer with a relatively thin extruded layer of occlusive hydrocolloid surrounding a thicker hydrocolloid disc. U.S. Pat. No 5,133,821 describes a process using a contouring roller to yield a hydrocolloid wound dressing. U.S. Pat. No. 5,716,475 describes a process for compression molding adhesive to yield a non-uniform thickness skin barrier. U.S. Pat. No. 5,811,116 describes embossing an adhesive, and U.S. Pat. No. 5,834,009 describes a contoured adhesive wafer with a thin peripheral section and a thick body section. Finally, U.S. Pat. No. 5,935,363 describes essentially a calendering process for producing shaped wafers.

It is believed these disclosures and others in the prior art all rely on thermoplastic methods of processing where the adhesive is heated and shaped to its final configuration before it is cooled. It has been found that the physical dimensions of the hydrocolloid powders establish a lower limit for the thickness of useful adhesives that can be produced by these processes. As the thickness of the adhesive decreases below about 0.010 inch thick it becomes more and more difficult to attain a uniform, continuous and useful layer of adhesive. The hydrocolloid powders interfere with flow of the adhesive and cause discontinuities in the product. They can stick out as lumps and interfere with the skin contacted needed for good adhesion. They can tear openings in the in-process adhesive. Below about 0.010 inch thick the adhesive has limited fluidity and strength and will not recover from these defects. It is believed that this reason explains why hydrocolloid adhesives produced by thermoplastic processes are not commercially available below a thickness of about 0.010 inch.

As previously mentioned U.S. Pat. No. 4,775,374 discloses an ostomy wafer wherein a relatively thick disc of hydrocolloid adhesive is surrounded by a thinner tape-like adhesive attached at its perimeter. According to the patent the tape-like adhesive disclosed can be of the acrylic type as in U.S. Pat No. 3,12,021, but is preferably made from the same hydrocolloid adhesive as the central disk component of the ostomy wafer. The microporosity of the thin adhesive further distinguishes it from the thicker adhesive, which is occlusive. The difference in permeability is explained to arise from a difference in processing methods. For both the acrylic and the hydrocolloid based formulations of the adhesive tape disclosed in '374 the need for microporosity results from the requirement that adhesive must manage perspiration to remain securely attached to the skin for extended wearing times. Neither the acrylic nor the hydrocolloid formulation will absorb an appreciable amount of moisture. Both rely of transmission of perspiration through the thickness of the device for their bond strength.

One limitation of the microporous nature of these adhesives is that they do not resist moisture from external sources well. For example, during bathing or showering water easily permeates through the adhesive backing and the adhesive itself. As a result, the tape collar can be overwhelmed with moisture at its interface with the skin, and the bond will fail. Very thin, microporous, hydrocolloid adhesives are especially vulnerable to this failure mode as they are water-loving structures that will quickly become saturated.

The process for imparting porosity to the hydrocolloid adhesive tape was a solvent coating process. The final desired formulation is blended into a suitable solvent to form a slurry. The slurry is then coated onto a carrier web using a knife over roll process. In that process thickness is controlled by adjusting the proximity of the knife to the roll, and by controlling the speed of the roll and the viscosity of the slurly. The carrier web then takes the coating through a series of ovens where nearly all of the solvent is driven off by heat. The solvent forms bubbles that burst leaving the solvent to flash out of the adhesive slurry. The process can be operated to affect the evaporation rate and viscosity of remaining adhesive so that the size and number of pores in the adhesive can be adjusted and controlled. Additionally, the carrier web, typically the adhesive's release liner, can also have volatile components that may flash from that substrate during the curing process. Accordingly the process must take into account the substrates potential effect on the porosity of the resulting adhesive.

DETAILED DESCRIPTION OF THE EMBODIMENTS

In contrast with the prior art, the present invention is an occlusive hydrocolloid adhesive coating that is between about 0.0027 and 0.007 inches thick, which contains at least 30% hydrocolloid powders, and is substantially free from voids caused by either the hydrocolloids or by evaporation of volatile. As a result, this adhesive is not microporous but instead is occlusive. Surprisingly, it has been found that these thin, occlusive hydrocolloid adhesives achieved a reliable wear time of 3 days as the component of an ostomy wafer, despite their lack of a microporous structure for evaporating perspiration. It has also been found that interspersing an impermeable, volatile free layer of process web between the adhesive coating and the volatile containing substrate will reduce the amount of voids contributed to the final coating by the carrier web.

The adhesive layer comprises a pressure sensitive rubbery clastomer material having intimately dispersed therein one or more water-soluble or water swellable hydrocolloids. Suitable rubbery clastomers include natural or synthetic viscous gum-like substances such as silicone rubber, butyl rubber, ethylene-propylene rubber, acrylonitrile rubber, polyurethane rubber, polyisobutylenes, styrenic block copolymers, etc. Suitable hydrocolloids include guar gum, sodium carboxymethylcellulose, cross-linked sodium carboxymethylcellulose, various starches, pectin, gelatin, alginic acid, locust bean gum, etc. The viscous gum-like substance acts as a binder for the hydrocolloid particles and, in addition, renders the final adhesive layer tacky, elastic, and pliable. The adhesive layer can also include up to about 35% by weight of one or more tackifiers, plasticizers or solvents, antioxidants, and preservatives. Suitable plasticizers such as mineral oil or petrolatum, or other low molecular polymers such as waxes, polyethylene, polypropylene, polybutene, and their copolymers, and other low molecular weight polyolefins. Mineral oil is preferred. Suitable tackifiers include aliphatic, aromatic, or hydrogenated hydrocarbon based synthetic tackifier resins and their mixtures. Tackifiers derived from natural sources are also possible but the synthetic aliphatic ones are preferred. The formulation may optionally include antioxidants for protection during processing and improved shelf life.

The hydrocolloid or mixture of hydrocolloid should comprise from about 20% to 65% by weight of the adhesive layer, preferably from about 30% to about 60% by weight of the adhesive layer. The clastomeric materials should comprise from about 30% to 60% by weight of the adhesive layer, preferably from about 35% to 50% by weight of the adhesive layer.

The microporous tape of this invention is prepared by dispersing the various components of the adhesive layer, i.e., the hydrocolloids, rubbery elastomers, tackifiers, plasticizers, antioxidants in a hydrocarbon solvent such as toluene, heptane, or hexane or mixtures thereof to form a slurry. The slurry is then deposited, for example, by means of a knife-over-roller, onto a web of silicone coated release paper. The slurry is deposited at a wet thickness of from about 5 mils to about 40 mils, preferably about 10 mils thick. The release paper having the adhesive layer is then passed through a drying tunnel, for example, a multi-zone hot air oven, where it is dried to less than 2% by weight of residual solvent. The air temperature and velocity through the drying zone are controlled so the adhesive layer is essentially continuous, smooth and free from pores. The dry adhesive layer is then laminated to a web of suitable backing material positioned so that the adhesive layer is pressed into intimate contact with the backing material. Backing materials may include films, foams and fabrics. The silicone coated release paper may be left on the resulting tape or it may be stripped off entirely. Irradiation or other techniques can be used to sterilize the final tape.

The porosity is determined by ASTM D-726-71 method using Gurley Densometer 4110 at 4.89 inches of water. An occlusive coating is one measuring less that about 1 cc/sec/in$^2$.

What is claimed is:

1. A pressure sensitive adhesive tape comprising a backing layer, and an occlusive adhesive layer coating laminated to said backing layer, said adhesive layer coating comprising from about 30% to about 60% by weight of a rubbery elastomer selected from the group consisting of silicone rubber, butyl rubber, ethylene-propylene rubber, acrylonitrile rubber, polyurethane rubber, styrenic block copolymers, and polyisobutylene, from about 20% to about 65% by weight of one or more water soluble or water swellable hydrocolloids selected from the group consisting of guar gum, starch sodium carboxymethylcellulose, cross-linked sodium carboxymethylcellulose, pectin, gelatin, alginic acid, locust bean gum, and up to 35% by weight of one or more tackifiers, plasticizers, and antioxidants; said adhesive layer coating being from about 0.0025 to about 0.007 inches thick and said adhesive layer coating being occlusive with a porosity less than about 1 cc/sec/in$^2$.

2. The tape of claim 1 wherein said adhesive layer coating comprises from about 35% to 50% by weight of said rubbery elastomer, from about 30% to about 60% by weight of said hydrocolloid or mixtures of hydrocolloids, and up to 35% by weight of said mixture of tackifiers, plasticizers, and antioxidants.

3. The tape of claim 2 wherein said backing layer is a woven or non-woven fabric, an open mesh polymeric substance, a film, or a polymeric foam.

4. The tape of claim 3 wherein said rubbery eleastomer is one or more polyisobutylenes.

5. The tape of claim 4 wherein said hydrocolloid is a mixture of sodium carboxymethylcellulose, pectin, and gelatin.

6. The tape of claim 5 wherein said hydrocolloid is a mixture of sodium carboxymethylcellulose, and gelatin.

7. The tape of claim 6 wherein said backing layer is non-woven fabric.

8. The tape of claim 1 wherein said adhesive layer coating comprises about 18% by weight of sodium carboxymethylcellulose, about 15% by weight of gelatin, about 38% by weight of polyisobutylenes, about 20% by weight of aliphatic tackifying resin, about 8.5% by weight of mineral oil, and about 0.5% by weight of antioxidant.

9. The tape of claim 8 wherein said adhesive layer coating is 0.003 inches thick and has a porosity of less than about 1 $cc/sec/in^2$.

10. The tape of claim 1 further comprising a silicone coated release paper on said adhesive layer coating wherein said adhesive layer coating has been deposited as a slurry on said silicone release paper and dried thereon.

* * * * *